(12) United States Patent
Bornzin et al.

(10) Patent No.: US 9,017,341 B2
(45) Date of Patent: Apr. 28, 2015

(54) MULTI-PIECE DUAL-CHAMBER LEADLESS INTRA-CARDIAC MEDICAL DEVICE AND METHOD OF IMPLANTING SAME

(75) Inventors: Gene A. Bornzin, Simi Valley, CA (US); John W. Poore, South Pasadena, CA (US); Zoltan Somogyi, Simi Valley, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 191 days.

(21) Appl. No.: 13/352,005

(22) Filed: Jan. 17, 2012

(65) Prior Publication Data

US 2013/0110127 A1    May 2, 2013

Related U.S. Application Data

(60) Provisional application No. 61/553,825, filed on Oct. 31, 2011.

(51) Int. Cl.
*A61B 19/00* (2006.01)
*A61N 1/05* (2006.01)
(Continued)

(52) U.S. Cl.
CPC ........... *A61N 1/0573* (2013.01); *A61N 1/37288* (2013.01); *A61N 1/3756* (2013.01); *A61N 1/36521* (2013.01)

(58) Field of Classification Search
CPC ... A61N 1/375; A61N 1/3752; A61N 1/3754; A61N 1/3756; A61N 1/3758; A61N 1/3968
USPC .................. 607/27, 61, 119, 122–123, 36–38; 439/131, 578, 638–639; 128/898, 899
See application file for complete search history.

(56) References Cited

U.S. PATENT DOCUMENTS

| 3,835,864 A | 9/1974 | Rasor et al. |
| 3,835,869 A | 9/1974 | Newman et al. |

(Continued)

FOREIGN PATENT DOCUMENTS

| EP | 1844812 A1 | 10/2007 |
| WO | 2005092431 A1 | 10/2005 |

(Continued)

OTHER PUBLICATIONS

Asirvatham, Samuel J. MD et al., "Intramyocardial Pacing and Sensing for the Enhancement of Cardiac Stimulation and Sensing Specificity," Pace. 2007;30:748-754.

(Continued)

*Primary Examiner* — Darwin Erezo
*Assistant Examiner* — Sidharth Kapoor

(57) ABSTRACT

A leadless intra-cardiac medical device (LIMD) includes an electrode assembly configured to be anchored within a first wall portion of a first chamber of a heart. The electrode assembly includes an electrode main body having a first securing helix, an electrode wire segment extending from the body, and a first segment-terminating contact positioned on the electrode wire segment. The device further includes a housing assembly configured to be anchored within a second wall portion of a second chamber of the heart. The housing assembly includes a body having a second securing helix, a housing wire segment extending from the body, and a second segment-terminating contact positioned on the housing wire segment. The device also includes a connector block that electrically connects the electrode wire segment to the housing wire segment by retaining the first and second segment-terminating contacts.

19 Claims, 9 Drawing Sheets

(51) Int. Cl.
*A61N 1/375* (2006.01)
*A61N 1/372* (2006.01)
*A61N 1/365* (2006.01)

(56) References Cited

U.S. PATENT DOCUMENTS

| | | | |
|---|---|---|---|
| 3,943,936 A | 3/1976 | Rasor et al. | |
| 4,987,897 A | 1/1991 | Funke | |
| 5,193,540 A | 3/1993 | Schulman et al. | |
| 5,358,514 A | 10/1994 | Schulman et al. | |
| 5,405,367 A | 4/1995 | Schulman et al. | |
| 5,411,535 A | 5/1995 | Fujii et al. | |
| 5,487,758 A | 1/1996 | Hoegnelid et al. | |
| 5,545,201 A | 8/1996 | Helland et al. | |
| 5,679,022 A | 10/1997 | Cappa et al. | |
| 5,814,089 A | 9/1998 | Stokes et al. | |
| 5,968,082 A * | 10/1999 | Heil | 607/37 |
| 6,096,064 A * | 8/2000 | Routh | 607/9 |
| 6,141,588 A | 10/2000 | Cox et al. | |
| 6,164,284 A | 12/2000 | Schulman et al. | |
| 6,181,965 B1 | 1/2001 | Loeb et al. | |
| 6,185,452 B1 | 2/2001 | Schulman et al. | |
| 6,208,894 B1 | 3/2001 | Schulman et al. | |
| 6,434,428 B1 | 8/2002 | Sloman et al. | |
| 6,754,536 B2 | 6/2004 | Swoyer et al. | |
| 7,047,076 B1 | 5/2006 | Li et al. | |
| 7,082,336 B2 | 7/2006 | Ransbury et al. | |
| 7,114,502 B2 | 10/2006 | Schulman et al. | |
| 7,305,267 B2 * | 12/2007 | Hector | 607/37 |
| 7,363,087 B2 | 4/2008 | Nghiem et al. | |
| 7,383,091 B1 | 6/2008 | Chitre et al. | |
| 7,513,257 B2 | 4/2009 | Schulman et al. | |
| 7,563,142 B1 * | 7/2009 | Wenger et al. | 439/669 |
| 7,565,195 B1 | 7/2009 | Kroll et al. | |
| 7,634,313 B1 | 12/2009 | Kroll et al. | |
| 7,643,872 B2 | 1/2010 | Min et al. | |
| 7,801,626 B2 | 9/2010 | Moser | |
| 7,860,570 B2 | 12/2010 | Whitehurst et al. | |
| 7,894,915 B1 * | 2/2011 | Chitre et al. | 607/123 |
| 7,899,555 B2 | 3/2011 | Morgan et al. | |
| 7,937,148 B2 | 5/2011 | Jacobson | |
| 7,945,333 B2 | 5/2011 | Jacobson | |
| 8,010,209 B2 | 8/2011 | Jacobson | |
| 8,032,219 B2 | 10/2011 | Neumann et al. | |
| 2004/0015204 A1 | 1/2004 | Whitehurst et al. | |
| 2004/0015205 A1 | 1/2004 | Whitehurst et al. | |
| 2004/0147973 A1 | 7/2004 | Hauser | |
| 2004/0201947 A1 * | 10/2004 | Stevenson et al. | 361/302 |
| 2006/0009831 A1 | 1/2006 | Lau et al. | |
| 2006/0020296 A1 * | 1/2006 | Fioretti | 607/37 |
| 2006/0085039 A1 * | 4/2006 | Hastings et al. | 607/9 |
| 2006/0135999 A1 | 6/2006 | Bodner et al. | |
| 2007/0055310 A1 | 3/2007 | Lau | |
| 2007/0088396 A1 | 4/2007 | Jacobson | |
| 2007/0088400 A1 | 4/2007 | Jacobson | |
| 2008/0097566 A1 * | 4/2008 | Colliou | 607/122 |
| 2008/0255647 A1 | 10/2008 | Jensen et al. | |
| 2009/0082828 A1 | 3/2009 | Ostroff | |
| 2009/0299433 A1 | 12/2009 | Dingman et al. | |
| 2010/0010381 A1 | 1/2010 | Skelton et al. | |
| 2010/0198288 A1 | 8/2010 | Ostroff | |
| 2011/0071586 A1 | 3/2011 | Jacobson | |
| 2011/0077708 A1 | 3/2011 | Ostroff | |
| 2011/0208260 A1 | 8/2011 | Jacobson | |
| 2011/0218587 A1 | 9/2011 | Jacobson | |
| 2011/0238077 A1 | 9/2011 | Wenger | |
| 2011/0251660 A1 | 10/2011 | Griswold | |
| 2011/0251662 A1 | 10/2011 | Griswold et al. | |
| 2012/0309237 A1 * | 12/2012 | Marzano et al. | 439/675 |

FOREIGN PATENT DOCUMENTS

| | | |
|---|---|---|
| WO | 2007047681 A2 | 4/2007 |
| WO | 2007047681 A3 | 9/2008 |
| WO | 2009039400 A1 | 3/2009 |
| WO | 2009078751 A1 | 6/2009 |
| WO | 2010088687 A1 | 8/2010 |

OTHER PUBLICATIONS

Brinker, Jeffrey A., "Endocardial Pacing Leads: The Good, the Bad, and the Ugly," Pace. 1995;18(Pt 1):953-954.

Calvagna, Giuseppe M. et al., "A complication of pacemaker lead extraction: pulmonary embolization of an electrode fragment," Europace. 2010;12:613.

Da Costa, Sergio Sidney Do Carmo et al., "Incidence and Risk Factors of Upper Extremity Deep Vein Lesions After Permanent Transvenous Pacemaker Implant: A 6-Month Follow-up Prospective Study," Pace. 2002;25:1301-1306.

Hauser, Robert G. et al., "Deaths and cardiovascular injuries due to device-assisted implantable cardioverter-defibrillator and pacemaker lead extraction," Europace. 2010;12:395-401.

Heaven, D.J. et al., "Pacemaker lead related tricuspid stenosis: a report of two cases," Heart. 2000;83:351-352.

Henz, Benhur D. MD et al., "Synchronous Ventricular Pacing without Crossing thetricuspid Valve or Entering the Coronary Sinus—Preliminary Results," J Cardiovasc Electrophysiol. (Dec. 2009);20:1391-1397.

Hesselson, Aaron B. Bsee et al., "Deleterious Effects of Long-Term Single-chamber Ventricular Pacing in Patients With Sick Sinus Syndrome: The Hidden Benefits of dual-Chamber Pacing," J Am Coll Cardiol. 1992;19:1542-1549.

Klug, Didier MD et al., "Systemic Infection Related to Endocardities on Pacemaker Leads—Clinical Presentation and Management," Circulation. 1997;95:2098-2107.

Korkeila, Petri et al., "Clinical and laboratory risk factors of thrombotic complications after pacemaker implantation: a prospective study," Europace. 2010;12:817-824.

Marrie, Thomas J. MD et al., "A Scanning and Transmission Electron Microscopic Study of an Infected Endocardial Pacemaker Lead," Circulation. 1982;66(6):1339-1341.

Menozzi, Carlo et al., "Intrapatient Comparison Between Chronic VVIR and DDD pacing in Patients Affected by High Degree AV Block Without Heart Failure," Pace. (Dec. 1990—Pt II);13:1816-1822.

Stellbrink, Christoph et al., "Technical considerations in implanting left ventricular pacing leads for cardiac resynchronization therapy," European Heart Journal Supplements. 2004;6(Supp D):D43-D46.

Stickler, J. William PhD, "Totally Self-Contained Intracardiac Pacemaker," J Electrocardiology. 1970;3(3-4):325-331.

Van Rooden, Cornelis J. MD et al., "Incidence and Risk Factors of Early Venous Thrombosis Associated with Permanent Pacemaker Leads," J Cardiovasc Electrophysiol. (Nov. 2004);15:1258-1262.

Vardas, P.E. et al., "A Miniature Pacemaker Introduced Intravenously and Implanted Endocardially. Preliminary Findings from an Experimental Study," Eur J Card Pacing Electrophysiol. 1991;1:27-30.

Voet, J.G. et al., "Pacemaker lead infection: report of three cases and review of the literature," Heart. 1999;81:88-91.

Walters, M.I. et al., "Pulmonary Embolization of a Pacing Electrode Fragment Complicating Lead Extraction," Pace. 1999;22:823-824.

* cited by examiner

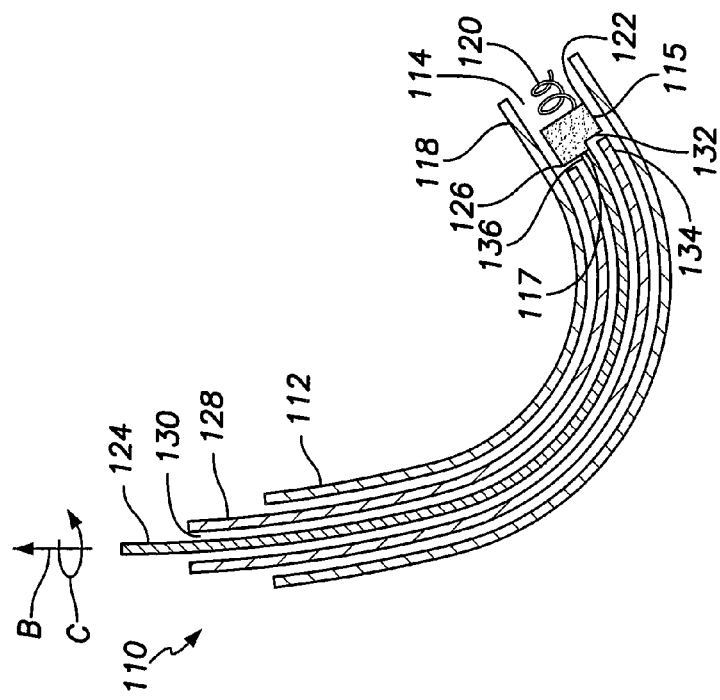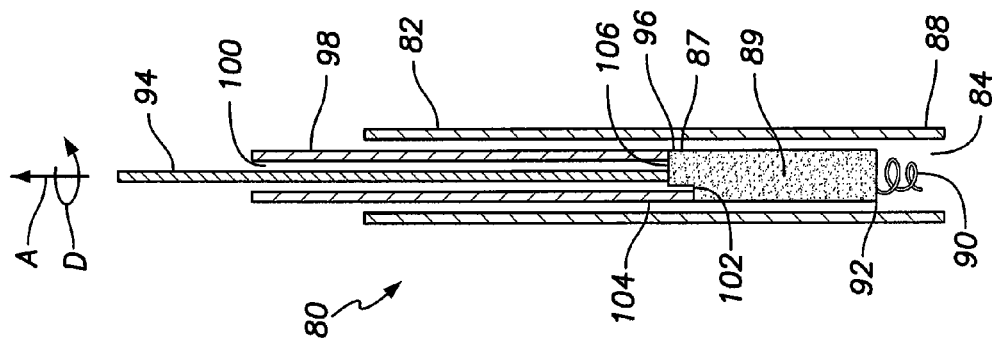

MULTI-PIECE DUAL-CHAMBER LEADLESS INTRA-CARDIAC MEDICAL DEVICE AND METHOD OF IMPLANTING SAME

CROSS REFERENCE TO RELATED APPLICATIONS

This application relates to and claims priority benefits from U.S. Provisional Application No. 61/553,825, filed Oct. 31, 2011, entitled "Intra-Cardiac Dual Chamber System and Method of Implanting Same," which is hereby incorporated by reference in its entirety. This application also relates to U.S. patent application Ser. No. 13/352,167, filed Jan. 17, 2012, entitled "Unitary Dual-Chamber Leadless Intra-Cardiac Medical Device and Method of Implanting Same", and Ser. No. 13/352,136, filed Jan. 17, 2012, entitled "Dual-Chamber Leadless Intra-Cardiac Medical Device with Intra-Cardiac Extension", which are hereby incorporated by reference in their entirety.

FIELD OF THE INVENTION

Embodiments of the present invention generally relate to implanted medical devices, and more particularly to multi-piece, dual-chamber leadless intra-cardiac medical devices and methods of implanting such devices entirely within a heart of a patient. As used herein, the term "leadless" generally refers to an absence of electrically-conductive leads that traverse vessels outside of the intra-cardiac space, while "intra-cardiac" means generally, entirely within the heart and associated vessels, such as the SVC, IVC, CS, pulmonary arteries and the like.

BACKGROUND OF THE INVENTION

Current implantable medical devices for cardiac applications, such as pacemakers, include a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker functionality. The leads traverse blood vessels between the can and heart chambers in order to position one or more electrodes carried by the leads within the heart, thereby allowing the device electronics to electrically excite or pace cardiac tissue and measure or sense myocardial electrical activity.

To sense atrial cardiac signals and to provide right atrial chamber stimulation therapy, the can is coupled to an implantable right atrial lead including at least one atrial tip electrode that typically is implanted in the patient's right atrial appendage. The right atrial lead may also include an atrial ring electrode to allow bipolar stimulation or sensing in combination with the atrial tip electrode.

Before implantation of the can into a subcutaneous pocket of the patient, however, an external pacing and measuring device known as a pacing system analyzer (PSA) is used to ensure adequate lead placement, maintain basic cardiac functions, and evaluate pacing parameters for an initial programming of the device. In other words, a PSA is a system analyzer that is used to test an implantable device, such as an implantable pacemaker.

To sense the left atrial and left ventricular cardiac signals and to provide left-chamber stimulation therapy, the can is coupled to the "coronary sinus" lead designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead is designed to: receive atrial and/or ventricular cardiac signals; deliver left ventricular pacing therapy using at least one left ventricular tip electrode for unipolar configurations or in combination with left ventricular ring electrode for bipolar configurations; deliver left atrial pacing therapy using at least one left atrial ring electrode as well as shocking therapy using at least one left atrial coil electrode.

To sense right atrial and right ventricular cardiac signals and to provide right-chamber stimulation therapy, the can is coupled to an implantable right ventricular lead including a right ventricular (RV) tip electrode, a right ventricular ring electrode, a right ventricular coil electrode, a superior vena cava (SVC) coil electrode, and so on. Typically, the right ventricular lead is inserted transvenously into the heart so as to place the right ventricular tip electrode in the right ventricular apex such that the RV coil electrode is positioned in the right ventricle and the SVC coil electrode will be positioned in the right atrium and/or superior vena cava. Accordingly, the right ventricular lead is capable of receiving cardiac signals, and delivering stimulation in the form of pacing and shock therapy to the right ventricle.

Although a portion of the leads are located within the heart, a substantial portion of the leads, as well as the IMD itself are outside of the patient's heart. Consequently, bacteria and the like may be introduced into the patient's heart through the leads, as well as the IMD, thereby increasing the risk of infection within the heart. Additionally, because the IMD is outside of the heart, the patient may be susceptible to Twiddler's syndrome, which is a condition caused by the shape and weight of the IMD itself. Twiddler's syndrome is typically characterized by a subconscious, inadvertent, or deliberate rotation of the IMD within the subcutaneous pocket formed in the patient. In one example, a lead may retract and begin to wrap around the IMD. Also, one of the leads may dislodge from the endocardium and cause the IMD to malfunction. Further, in another typical symptom of Twiddler's syndrome, the IMD may stimulate the diaphragm, vagus, or phrenic nerve, pectoral muscles, or brachial plexus. Overall, Twiddler's syndrome may result in sudden cardiac arrest due to conduction disturbances related to the IMD.

In addition to the foregoing complications, implanted leads may experience certain further complications, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

To combat the foregoing limitations and complications, small sized devices configured for intra-cardiac implant have been proposed. These devices, termed leadless pacemakers (LLPM) are typically characterized by the following features: they are devoid of leads that pass out of the heart to another component, such as a pacemaker can outside of the heart; they include electrodes that are affixed directly to the can of the device; the entire device is attached to the heart; and the device is capable of pacing and sensing in the chamber of the heart where it is implanted.

LLPM devices that have been proposed thus far offer limited functional capability. These LLPM devices are able to sense in one chamber and deliver pacing pulses in that same chamber, and thus offer single chamber functionality. For example, an LLPM device that is located in the right atrium would be limited to offering AAI mode functionality. An AAI mode LLPM can only sense in the right atrium, pace in the right atrium and inhibit pacing function when an intrinsic event is detected in the right atrium within a preset time limit. Similarly, an LLPM device that is located in the right ventricle would be limited to offering VVI mode functionality. A VVI mode LLPM can only sense in the right ventricle, pace in the right ventricle and inhibit pacing function when an intrinsic event is detected in the right ventricle within a preset time limit. To gain widespread acceptance by clinicians, it would be highly desired for LLPM devices to have dual chamber pacing/sensing capability (DDD mode) along with other features, such as rate adaptive pacing.

It has been proposed to implant sets of multiple LLPM devices within a single patient, such as one or more LLPM devices located in the right atrium and one or more LLPM devices located in the right ventricle. The atrial LLPM devices and the ventricular LLPM devices wirelessly communicate with one another to convey pacing and sensing information there between to coordinate pacing and sensing operations between the various LLPM devices.

However, these sets of multiple LLPM devices experience various limitations. For example, each of the LLPM devices must expend significant power to maintain the wireless communications links. The wireless communications links should be maintained continuously in order to constantly convey pacing and sensing information between, for example, atrial LLPM device(s) and ventricular LLPM device(s). This pacing and sensing information is necessary to maintain continuous synchronous operation, which in turn draws a large amount of battery power.

Further, it is difficult to maintain a reliable wireless communications link between LLPM devices. The LLPM devices utilize low power transceivers that are located in a constantly changing environment within the associated heart chamber. The transmission characteristics of the environment surrounding the LLPM device change due in part to the continuous cyclical motion of the heart and change in blood volume. Hence, the potential exists that the communications link is broken or intermittent.

SUMMARY OF THE INVENTION

Certain embodiments provide leadless intra-cardiac medical device (LIMD) configured to be contained within a heart of a patient. The device includes an electrode assembly configured to be anchored within a first wall portion of a first chamber of a heart. The electrode assembly includes an electrode main body having a first securing helix, an electrode wire segment extending from the body, and a first segment-terminating contact positioned on the electrode wire segment. The device further includes a housing assembly configured to be anchored within a second wall portion of a second chamber of the heart. The housing assembly includes a body having a second securing helix, a housing wire segment extending from the body, and a second segment-terminating contact positioned on the housing wire segment. The device also includes a connector block that electrically connects the electrode wire segment to the housing wire segment by retaining the first and second segment-terminating contacts.

The connector block may include recessed channels having openings. The first and second segment-terminating contacts pass through the openings into the recessed channels. Each of the first and second segment-terminating contacts may include a connection stud that is retained within a contact-receiving member of the connector block. Each of the connection studs may include an expanded head integrally connected to a clamping tail. The electrode, the first segment-terminating contact, the housing, the second segment-terminating contact, and the connector block may all be within the heart of the patient.

Certain embodiments provide a method of implanting a leadless intra-cardiac medical device (LIMD). The method includes introducing an electrode into a first chamber of the heart, anchoring the electrode into a first wall portion of the first chamber, the electrode being coupled to a proximal end of an electrode wire segment having a segment-terminating contact at its dustal end; introducing a housing into a second chamber of the heart, anchoring the housing into a second wall portion of the second chamber, the housing being coupled to a proximal end of an housing wire segment having a segment-terminating contact at its distal end; and interconnecting the segment-terminating contacts with a connector block in order to electrically connect the electrode and the housing, the connector block remaining implanted inside the heart throughout operation of the device.

The connector block may include recessed channels having openings, and interconnecting may include forcing the segment-terminating contacts through the openings into the recessed channels.

Anchoring the electrode may include urging the electrode into the first wall portion with a pusher tool, rotating the pusher tool, wherein the rotating causes the electrode to rotate, and screwing the electrode into the first wall portion through the rotating until the electrode is securely anchored into the first wall portion. The method may also include removing the pusher tool from the electrode after the electrode is securely anchored into the first wall portion, the implanted electrode wire segment extending from the electrode to the pusher tool.

The method may also include joining a temporary electrode wire segment and a temporary housing wire segment to the electrode and housing wire segments, respectively, at the segment-terminating contacts; and connecting the temporary electrode wire segment and the temporary housing wire segment to a pacing system analyzer (PSA) to test the electrode and the housing. The method may also include disconnecting the temporary electrode and housing wire segments from the segment-terminating contacts within the first and second chambers of the heart.

Interconnecting may include pulling connection studs of the segment-terminating contacts into contact-receiving members of the connector block. The method may also include disconnecting the temporary electrode and housing wire segments from the segment-terminating contacts.

The anchoring the housing may include urging the housing into the second wall portion with a pusher tool, rotating the pusher tool, wherein the rotating causes the housing to rotate, and screwing the housing into the second wall portion through the rotating until the housing is securely anchored into the second wall portion. The disconnecting may include unscrewing the temporary electrode and housing wire segments from the segment-terminating contacts.

The pusher tool may include a protruding portion that is received by a reciprocal portion within the housing to ensure that rotation of the pusher tool causes a corresponding rotation in the housing. The pusher tool may be slidably retained within a main lumen.

The electrode may be introduced into the heart before the housing. Alternatively, the housing may be introduced into the heart before the electrode.

BRIEF DESCRIPTION OF THE DRAWINGS

FIG. 2 illustrates a longitudinal axial view of a housing assembly portion of a leadless intra-cardiac medical device (LIMD) within an introducer assembly.

FIG. 3 illustrates a longitudinal axial view of an electrode assembly portion of an LIMD within an introducer assembly.

FIG. 5A illustrates a sectional view of a connector block portion of an LIMD with elements of a housing assembly and electrode assembly passing there through.

DETAILED DESCRIPTION

Figure 1:
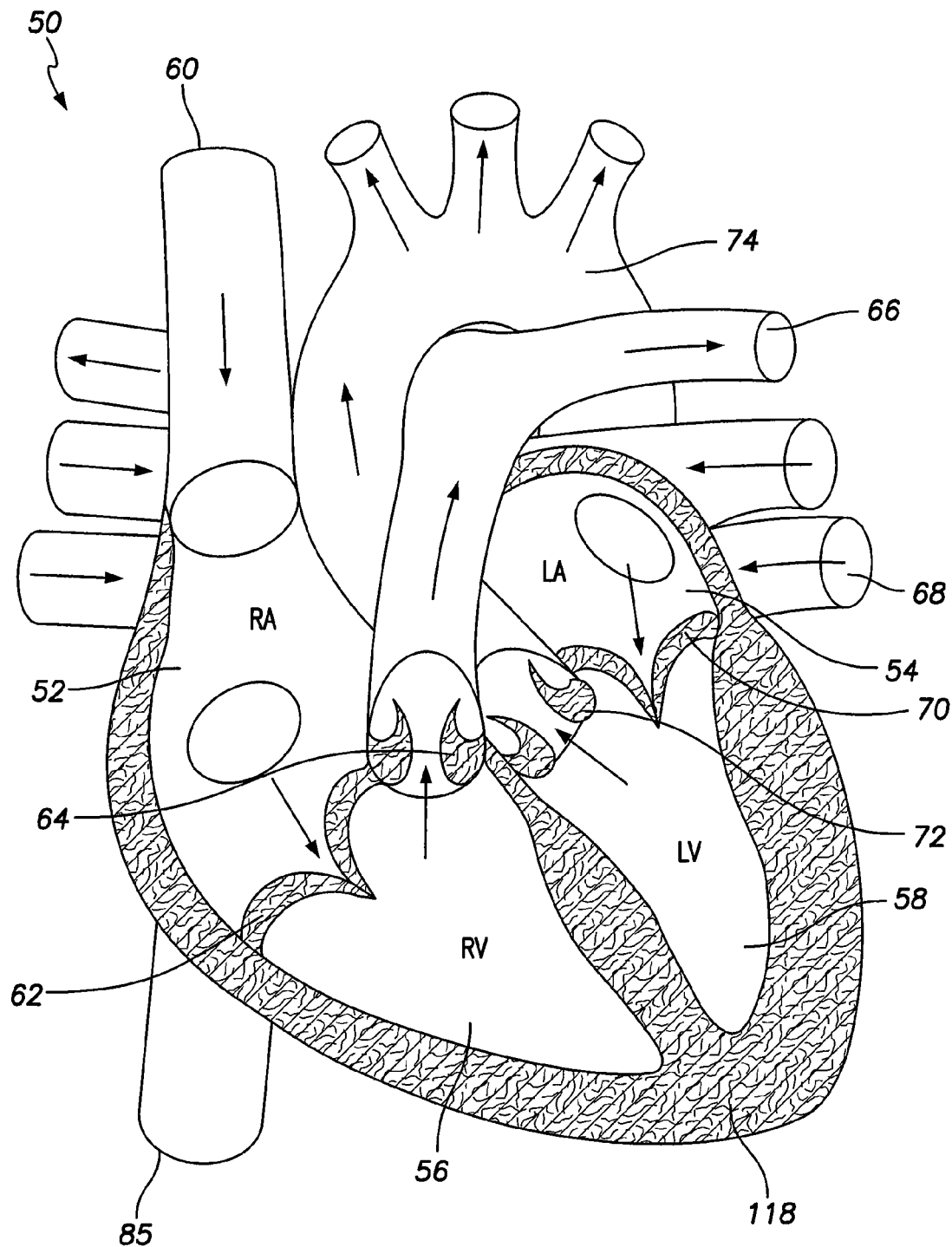
FIG. 1 illustrates a simplified view of a human heart.

FIG. 1 illustrates a simplified view of a human heart 50. The heart 50 is generally enclosed in a double-walled sac called a pericardium, which protects the heart 50. The outer wall of the heart includes three layers. The outer layer of the heart 50 is referred to as the epicardium, or visceral pericardium because it is also the inner layer of the pericardium. The middle layer of the heart 50 is referred to as the myocardium and is composed of muscle that contracts. The inner layer of the heart 50 is referred to as the endocardium and is in contact with blood that is pumped through the heart 50.

As shown in FIG. 1, the heart has four chambers, a right atrium 52, a left atrium 54, a right ventricle 56, and a left ventricle 58. In general, the atria 52, 54 are the receiving chambers, while the ventricles 56, 58 are the discharging chambers. Deoxygenated blood enters the heart 50 through the superior vena cava 60, for example, and passes into the right atrium 52. The blood is then pumped through the tricuspid valve 62 into the right ventricle 56 before being pumped out through the pulmonary valve 64 into the pulmonary artery 66. The blood is then oxygenated in the lungs and returns to the heart 50 through the pulmonary vein 68 into the left atrium 54, where it is then pumped through the mitral valve 70 and into the left ventricle 58. The oxygenated blood then travels from the left ventricle 58 through the aortic valve 72 and into the aorta 74, through which the oxygenated blood is then circulated throughout the body.

FIG. 2 illustrates a longitudinal axial view of a housing introducer assembly 80, according to an embodiment. The introducer assembly 80 includes a flexible, cylindrical, open-ended sheath 82 defining an internal introducer passage 84 and having an open distal end 88. The sheath 82 may be formed of various materials, including but not limited to silicon rubber. The sheath 82 is configured to be maneuvered through human vasculature, such as veins and arteries, and into the heart 50, by way of the superior vena cava 60 or the interior vena cava 85 (shown in FIG. 1).

A housing assembly 86 of a leadless intra-cardiac medical device (LIMD) is secured within the internal introducer passage 84 of the sheath 82 near a distal end 88. The housing assembly 86 includes a body 89 containing electronics that allow the LIMD to function as one of various types of implantable devices, such as, for example, an implantable pacemaker, a cardiac resynchronization therapy (CRT) device, an implantable cardioverter-defibrillator ("ICD"), neurostimulator, or the like. The LIMD may be configured for DDDR pacing (atrial and ventricular pacing, atrial and ventricular sensing, dual response and rate-adaptive, used for dual chamber pacemakers). A securing helix 90 extends from a distal end 92 of the housing assembly 86. The housing assembly 86 also includes a conductive wire 94 covered with insulation that extends from a proximal end 96 of the body 89. The conductive wire includes one or more electrical conductors that connect with electronics associated with the body 89. The securing helix 90 may be a coiled helical wire having a sharp distal end. All or a portion of the helix 90 may function as an electrode. Additional electrodes, such as ring electrodes, may be included on the body 89.

A pusher tool 98 is also positioned within the sheath 82. The pusher tool 98 is configured to slide through the sheath 82. The pusher tool 98 has an internal passage 100 into which the wire 94 passes. As shown in FIG. 2, the pusher tool 98 is generally a longitudinal tube or the like. Similarly, the sheath 82 is also a longitudinal tube having the open distal end 88. The pusher tool 98 is configured to be moved within the sheath 82. The pusher tool 98 is configured to slide, telescope, or otherwise move within the sheath 82.

A physician or surgeon operates the housing introducer assembly 80 at a proximal end (not shown). The proximal end may include controls that allow the sheath 82 and the pusher tool 98 to be bent, curved, canted, rotated, twisted, or the like, so as to be navigated through a patient's vasculature. In an embodiment, a distal end of the pusher tool 98 may be bent, curved, canted, rotated, twisted, articulated, or the like through operation by the physician or surgeon manipulating the proximal end of the assembly 80. Movement of the distal end of the pusher tool 98 causes a corresponding movement in the sheath 82. Optionally, the distal end 88 of the sheath 82 may be bent, curved, canted, rotated, twisted, articulated, or the like through manipulation of controls at the proximal end, which causes a corresponding movement in the pusher tool 98. One of both of the sheath 82 and/or the pusher tool 98 are configured to be moved in such a manner.

The pusher tool 98 abuts into the proximal end 96 of the body 89. As shown in FIG. 2, a pusher retention element 102, such as a notch, recess, divot, or the like is formed within the proximal end of the body 89. A retaining element 104, such as a tab, spur, barb, extension, or the like of the pusher tool 98 fits into the pusher retention element 102. Therefore, rotation of the pusher tool 98 causes a corresponding rotation of the housing assembly 86. Optionally, the pusher tool 98 may connect to the body 89 through various other interfaces that ensure synchronized rotation of the pusher tool 98 and the housing assembly 86.

In order to ensure that the pusher tool 98 remains securely abutted against the proximal end 96 of the body 89 while within the internal introducer passage 84 of the sheath 82, tension is applied to the wire 94 in the direction of arrow A. As tension is applied to the wire 94 in the direction of arrow A, the body 89 is forced in the same direction. Because the outer diameter of the body 89 exceeds the inner diameter of the pusher tool 98, the body 89 remains outside of the internal passage 100 of the pusher tool 98. That is, the body 89 does not pass into the pusher tool 98. Instead, a base 87 of the body 89 abuts against the distal end 106 of the pusher tool 98. As noted above, the retaining element 104 of the pusher tool 98 engages the pusher retention element 102 of the body 89, thereby ensuring that the body 89 does not rotate relative to the pusher tool 98. Instead, rotation of the pusher tool 98 and the housing assembly 86 is synchronized in that rotation of the pusher tool 98 causes a common rotation in the housing assembly 86.

FIG. 3 illustrates a longitudinal axial view of an electrode introducer assembly 110, according to an embodiment. The electrode introducer assembly 110 includes a flexible, cylindrical, open-ended sheath 112 defining an internal passage 114 having an open distal end 118. The sheath 112 may be formed of various materials, including but not limited to silicon rubber. The sheath 112 is configured to be maneuvered through human vasculature, such as veins and arteries, and into the heart 50, by way of the superior vena cava 60 or the interior vena cava 85 (shown in FIG. 1).

An electrode assembly 116 is secured within the internal passage 114 of the sheath 112 near a distal end 118 of the sheath 112. The electrode assembly 116 may be place within an atrium of a patient's heart, while the housing assembly 86 shown in FIG. 2 is positioned within a ventricle of the patient's heart. The electrode assembly 116 includes a body 115 and a conductive wire 124 covered in insulation that extends from a proximal end 126 of the body 115. The conductive wire includes one or more electrical conductors that connect with one or more electrodes associated with the body 115. A securing helix 120 extends from a distal end 122 of the electrode assembly 116. The securing helix 120 may be a coiled helical wire having a sharp distal end. All or a portion of the helix 120 may function as an electrode. Additional electrodes, such as ring electrodes, may be included on the body 115.

A pusher tool 128 is also positioned within the sheath 112. The pusher tool 128 is configured to slide through the sheath 112. The pusher tool 128 has an internal passage 130 into which the wire 124 passes. As shown in FIG. 3, the pusher tool 128 is generally a longitudinal tube or the like. Similarly, the sheath 112 is also a longitudinal tube having the open distal end 118. The pusher tool 128 is configured to be moved within the sheath 112. The pusher tool 128 is configured to slide, telescope, or otherwise move within the sheath 112.

A physician or surgeon operates the electrode introducer assembly 110 at a proximal end (not shown). The proximal end may include controls that allow the sheath 112 and the pusher tool 128 to be bent, curved, canted, rotated, twisted, or the like, so as to be navigated through a patient's vasculature. In an embodiment, a distal end of the pusher tool 128 may be bent, curved, canted, rotated, twisted, articulated, or the like through operation by the physician or surgeon manipulating the proximal end of the assembly 110. Movement of the distal end of the pusher tool 128 causes a corresponding movement in the sheath 112. Optionally, the distal end 118 of the sheath 112 may be bent, curved, canted, rotated, twisted, articulated, or the like through manipulation of controls at the proximal end, which causes a corresponding movement in the pusher tool 128. One of both of the sheath 112 and/or the pusher tool 128 are configured to be moved in such a manner.

The pusher tool 128 abuts into the proximal end 126 of the body 115. As shown in FIG. 3, a pusher retention element 132, such as a notch, recess, divot, or the like is formed within the proximal end of the body 115. A retaining element 134, such as a tab, spur, barb, extension, or the like of the pusher tool 128 fits into the pusher retention element 132. In this manner, rotation of the pusher tool 128 causes a corresponding rotation of the electrode assembly 116. Optionally, the pusher tool 128 may connect to the body 115 through various other interfaces that ensure synchronized rotation of the pusher tool 128 and the electrode assembly 116.

In order to ensure that the pusher tool 128 remains securely abutted against the proximal end 126 of the body 115 while within the internal introducer passage 114 of the sheath 112, tension is applied to the wire 124 in the direction of arrow B. As tension is applied to the wire 124 in the direction of arrow B, the body 115 is forced in the same direction. Because the outer diameter of the body 115 exceeds the inner diameter of the pusher tool 128, the body 115 remains outside of the internal passage 130 of the pusher tool 128. That is, the body 115 does not pass into the pusher tool 128. Instead, a base 117 of the body 115 abuts against the distal end 136 of the pusher tool 128. As noted above, the retaining element 134 of the pusher tool 128 engages the pusher retention element 132 of the body 115, thereby ensuring that the body 115 does not rotate relative to the pusher tool 128. Instead, rotation of the pusher tool 128 and the electrode assembly 116 is synchronized in that rotation of the pusher tool 128 causes a common rotation in the electrode assembly 116.

Figure 4:
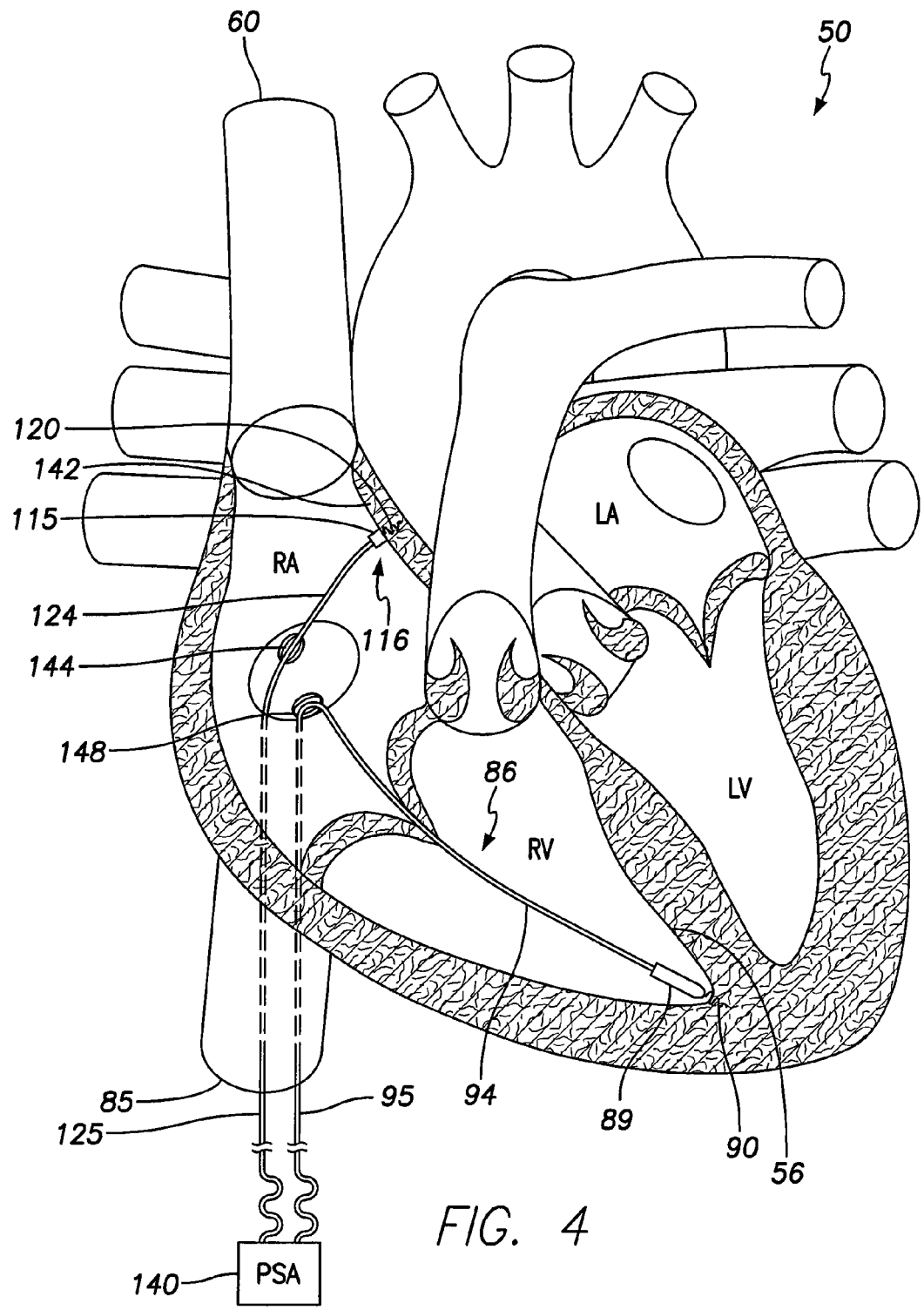
FIG. 4 illustrates a simplified diagram of an LIMD connected to a pacing system analyzer during implanted.

FIG. 4 illustrates a simplified diagram of the housing assembly 86 and the electrode assembly 116 implanted within the heart 50, according to an embodiment. Referring to FIGS. 2-4, in order to implant the housing assembly 86 and the electrode assembly 116 into the heat 50, each of the housing introducer assembly 80 and the electrode introducer assembly 110 are introduced into a vein of a patient. Either the housing introducer assembly 80 or the electrode introducer assembly 110 may be introduced into the vein first. During this time, a separate and distinct imaging system, such as a fluoroscopic imaging system, and/or a surgical navigation system may be used to assist in guiding the assemblies 80 and 110 into the heart 50. For example, a surgeon may view a real-time fluoroscopic image of the patient's anatomy to see the introducer assemblies 80, 110 being maneuvered through patient anatomy.

The introducer assemblies 80, 110 are maneuvered through the vein and ultimately into the inferior vena cava 85, for example, and into the right atrium 52. Optionally, the introducer assemblies 80, 110 may be maneuvered from a vein that connects to the superior vena cava 60 and into the right atrium 60. Again, as noted above, the introducer assemblies 80, 110 may be maneuvered into the heart at separate and distinct times. For example, the housing introducer assembly 80 may be maneuvered into the right atrium 52 before the electrode introducer assembly 110, or vice versa.

As shown in FIG. 4, the conductive wires 94 and 124 of the housing assembly 86 and the electrode assembly 116, respectively, are electrically connected to a pacing system analyzer (PSA) 140, through temporary wire segments 95, 125. The PSA is used to ensure adequate lead placement, maintain basic cardiac functions, and evaluate pacing parameters for the housing assembly 86 and the electrode assembly 116. In general, the PSA 140 is used to test the housing assembly 86 and the electrode assembly 116.

As mentioned above, the housing assembly wire 94 connects to a temporary housing assembly wire segment 95. Similarly, the electrode assembly wire 124 connects to a temporary electrode assembly wire segment 125. The temporary housing assembly wire segment 95 remains connected to the housing assembly wire 94 during installation and testing. Similarly, the temporary electrode assembly wire segment 125 remains connected to the electrode assembly wire 124 during installation and testing.

Referring again to FIGS. 1-4, the electrode assembly 116 is maneuvered into the right atrium so that the helix 120 is adjacent a right atrial appendage 142. The pusher tool 128 urges the helix 120 into the right atrial appendage 142. Once the helix 120 contacts the right atrial appendage 142, the pusher tool 128 is rotated by a physician at the proximal end of the assembly 110 in the direction of arc C (FIG. 3), which causes the pusher tool 128 to rotate, which, in turn, drives rotation of the electrode assembly 116 (shown in FIG. 3). Accordingly, the helix 120 rotates in the direction of arc C, while at the same time being urged into tissue in the right atrial appendage 142. As such, the electrode assembly 116 is screwed into the right atrial appendage 142. Once the electrode assembly 116 is firmly secured into tissue in the right atrial appendage 142, the pusher tool 128 is pulled away from the electrode assembly 116 in the direction of arrow B (FIG. 3). Because the electrode assembly 116 is now anchored into the right atrial appendage 142, the electrode assembly 116 remains secured thereto, while the pusher tool 128 separates and recedes away from the electrode assembly 116. Similarly, the sheath 112 is also pulled away in the direction of arrow B, leaving only the electrode assembly 116 and the wire 124 in the right atrium.

As shown in FIG. 4, the electrode assembly wire 124 includes a segment-terminating contact 144 that connects the temporary electrode assembly wire segment 125 to the electrode assembly wire 124. The segment-terminating contact 144 connects the wires together proximate the right atrial appendage 142. For example, the segment-terminating contact 144 may connect the wires at a distance from the right atrial appendage 142 that prevents the segment-terminating contact 144 from passing into the tricuspid valve 62. The remainder of the temporary electrode assembly wire segment 125 is then laid in the inferior vena cava 85, passing out through the vein, and to the PSA 140.

After, or before, the electrode assembly 116 is anchored into the right atrial appendage 142, the housing assembly 86 is anchored into the right ventricular apex 146. Referring again to FIGS. 1-4, the housing assembly 86 is maneuvered into the right atrium 52, down through the tricuspid valve 62 and into the right ventricle 56 so that the helix 90 is adjacent the right ventricular apex 146. The pusher tool 98 urges the helix 90 into tissue at the apex 146. Once the helix 90 contacts the apex 146, a physician rotates the proximal end of the pusher tool 98, which causes the pusher tool 98 to rotate in the direction of arc D (FIG. 2). Rotation of the pusher tool 98 drives rotation of the housing assembly 86. Accordingly, the helix 90 rotates in the direction of arc D, while at the same time being urged into the apex 146. As such, the housing assembly 86 is screwed into the apex 146. Once the housing assembly 86 is firmly secured into the apex 146, the pusher tool 98 is separated and pulled away from the housing assembly 86 in the direction of arrow A (shown in FIG. 2). Because the housing assembly 86 is now anchored into the apex 146, the housing assembly 86 remains secured thereto, while the pusher tool 98 separates and recedes away from the housing assembly 86. Similarly, the sheath 82 is also removed and pulled away in the direction of arrow A (FIG. 2), leaving only the housing assembly 86 in the right ventricle.

As shown in FIG. 4, the housing assembly wire 94 includes a segment-terminating contact 148 that connects the temporary housing assembly wire segment 95 to the implanted housing assembly wire 94. The segment-terminating contact 148 connects the wires together proximate the inferior vena cava 85. For example, the segment-terminating contact 148 may be connect the wires within the heart at a distance from the inferior vena cava 85 that prevents the segment-terminating contact 148 from passing into the tricuspid valve 62. The remainder of the housing assembly wire segment 95 is then laid in the inferior vena cava 85, passing out through the vein, and to the PSA 140.

Once the electrode assembly 116 and the housing assembly 86 are anchored in position and tested by the PSA 140, the temporary wire segments 95, 125 may be disconnected from the PSA 140. Once the temporary wire segments 95, 125 are disconnected from the PSA 140, a splicing member or connector block may be positioned onto proximal ends of the temporary wire segments 95, 125, respectively, and slid up the segments until they meet the segment-terminating contacts 144, 148. The connector block may be moved over the wire segments 95, 125 into the heart 50 by way of a separate pusher tool, or simply a separate and distinct wire that allows the connector block to be maneuvered into the heart 50.

Figure 5A:
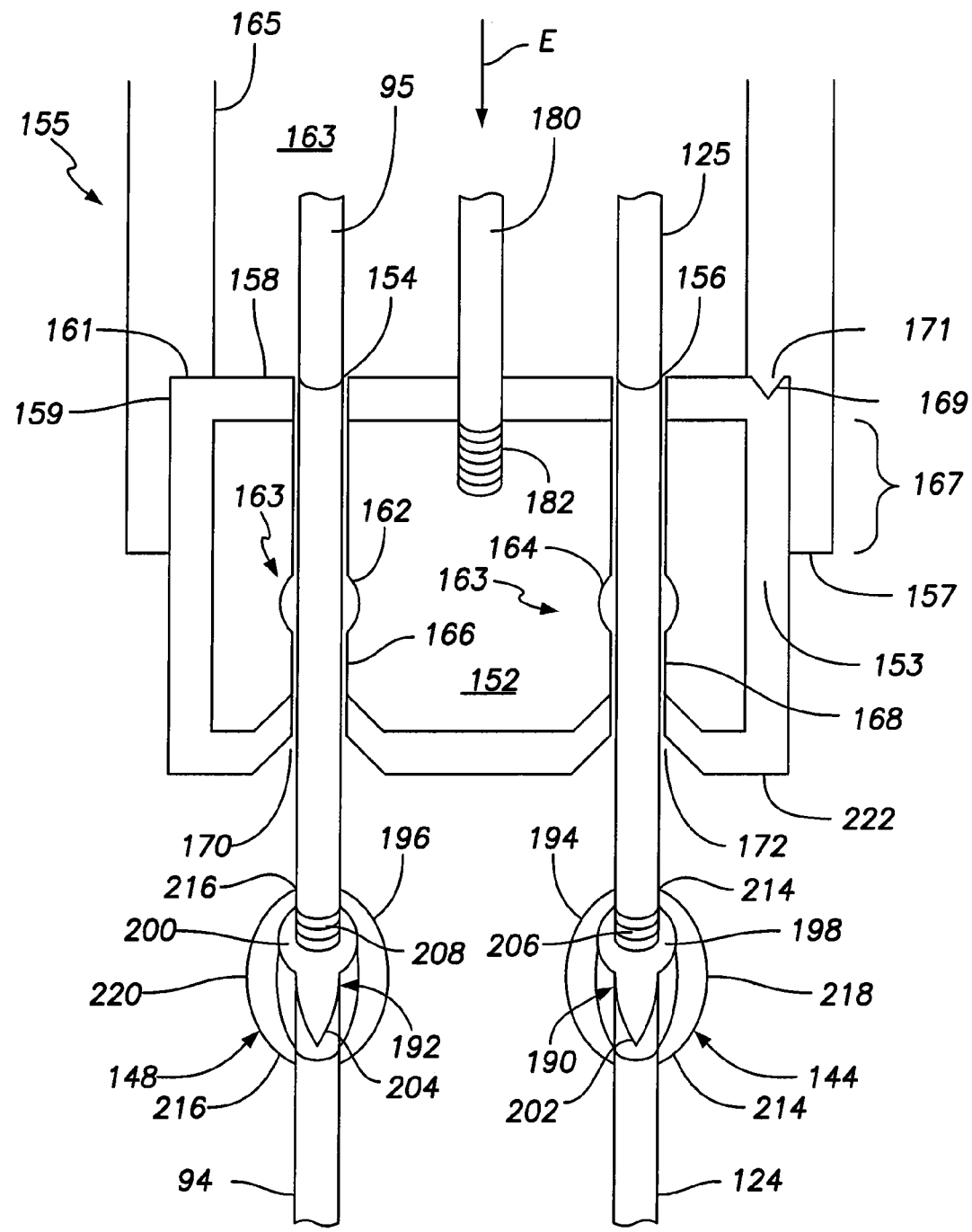

FIG. 5A illustrates a sectional view of a connector block 150 and the segment-terminating contacts 144, 148, of the housing assembly wire 94 and the electrode assembly wire 124. The connector block 150 or splicing member includes a main body 152, which may be formed of a conductive material, such as Titanium or stainless steel, covered by an insulative biocompatible material 153, such as silicon rubber, for example. The main body 152 includes wire passages 154, 156 at a proximal end 158. The wire passages 154, 156 slidably receive the temporary wire segments 95, 125, respectively. The wire passages 154, 156 lead into contact-receiving members within the body 152. The contact-receiving members represent flared chambers 163 that may include spring terminals or snap bulbs 162, 164, respectively, having expanded heads that are located and oriented toward the proximal end 158 of the connector block 150. The snap bulbs 162, 164 allow the wires 94, 124 to pass therein. The snap bulbs 162, 164, in turn, communicate directly with recessed channels 166, 168, respectively, having a smaller diameter than the snap bulbs 162, 164, respectively. The recessed channels 166, 168 are located and oriented toward a distal end 222 of the connector block 150. The recessed channels 166, 168 connect to wire openings 170, 172, respectively, that allow the temporary wire segments 95, 125 to pass therethrough. The openings 170, 172, wire passages 154, 156 and the opening 182 are formed as self-sealing septum to enclose the housing of the connector block 150 when items are within or removed from each opening or passage.

A maneuvering wire 180 connects to the distal end 158 of the main body 152 at a central threaded opening 182 that may be between the wire passages 154, 156 respectively. The maneuvering wire 180 threadably connects to the opening 182. The maneuvering wire 180 allows a surgeon to push and maneuver the connector block 150 over the temporary wire segments 95, 125 into the patient's heart. As the connector block 150 is pushed in the direction of arrow E, the wire segments 95, 125 slide through the main body 152.

Each segment-terminating contact 144, 148 includes a connection stud 190, 192, respectively, within a protective sheath 194, 196 or sleeve, respectively. Each connection stud 190, 192 includes an expanded head 198, 200 oriented toward the connector block 150, respectively, integrally connected to a smaller clamping tail 202, 204, respectively, oriented away from the connector block 150. The connection studs 190, 192 may be formed of Titanium, stainless steel, or the like. The heads 198, 200 include threaded channels 206, 208, respectively, that receive and threadably retain distal ends of the wires 125, 95, respectively. The clamping tails 202, 204 are each permanently secured to the conductive wire segments 210, 212, respectively. As shown, the temporary wire segments 95, 125 connect to the assembly wires 94, 124, respectively. However, as explained below, the temporary wire segments 95, 125 are configured to detach from the assembly wires 94, 124.

The protective sheaths 194, 196 or sleeves may be formed of soft silicone, rubber, or the like. The protective sheaths 194, 196 include tapered ends 214, 216, respectively, connected to expanded mid-sections 218, 220, respectively. The segment-terminating contacts 144, 148 are retained within the mid-sections 218, 220, respectively.

Referring to FIGS. 4 and 5A, as the connector block 150 is slid over the temporary wire segments 95, 125 toward the segment-terminating contacts 144, 148, the segment-terminating contacts 144, 148 cinch toward each other, as shown in FIG. 5A. The connector block 150 continues to be moved toward the segment-terminating contacts 144, 148. As the connector block 150 abuts the segment-terminating contacts 144, 148, the sheaths 194, 196, respectively, abut into the distal end 222 of the connector block 150. With continued urging of the connector block 150 in the direction of arrow E (shown in FIG. 5A), the connection studs 190, 192 slide out of the sheaths 194, 196, respectively, as the tension of the wires 94, 124 pulls the studs 190, 192 into the connector block 150. The sheaths 194, 196 are not rigid enough to pass through the wire openings 170, 172. However, the expanded heads 198, 200 move into the wire openings 172, 170, respectively, and flex the recessed channels 168, 166, respectively, open. The expanded heads 198, 200 are then snapably retained within the snap bulbs 164, 162, respectively. Accordingly, the assembly wires 94, 124 are effectively electrically spliced together through conductive elements (not shown), e.g., wires or traces, within the connector block.

After the connection studs 190, 192 are retained within the connection block 150, the sheaths 194, 196, respectively, simply hang on the assembly wires 124, 94, respectively, and the distal end 222 of the connection block 150. A portion of the sheaths 194, 196 may be compressed within the wires openings 172, 170, respectively, thereby ensuring that the sheaths 194, 196 do not slide down the wires 210, 212, respectively. However, because the sheaths 194, 196 may be formed of a non-rigid material, such as silicone or rubber, the sheaths 194, 196 may not be susceptible to sliding down the wires 210, 212, respectively.

After the connection studs 190, 192 are snapably secured within the connection block 150, the temporary wire segments 95, 125 may be manipulated to threadably disengage from the heads 200, 198, respectively. Then, the temporary wire segments 95, 125 may be removed from the connectors 148, 144, respectively. Similarly, the wire 180 may be manipulated to threadably disengage from the connector block 150 and be removed, leaving only a LIMD defined by the housing assembly 86 and the electrode assembly 116 that are conductively connected and/or spliced together through the connector block 150.

Alternatively, the segment-terminating contacts 144, 148 may connect to a joining mechanism other than the connector block 150. For example, the segment-terminating contacts 144, 148 may themselves be threaded members that connect to a threaded joint. Optionally, the segment-terminating contacts 144, 148 may be plug members that engage a connector member having reciprocal openings. Also, alternatively, the segment-terminating contacts 144, 148 may be shaped and sized to securely connect to various other reciprocal structures.

Optionally, the connector block 150 may be loaded into a catheter. In FIG. 5A a distal end 157 of a catheter 155 is illustrated. The catheter 155 may resemble a conventional catheter or resemble other existing tools used in other types of implants that has a proximal end with user controls that are adjusted by a physician, and a distal end that is configured to be manipulated in three dimensions (relative to the longitudinal axis of the introducer) in order to guide and navigate the distal end 157 of the catheter 155 to a desired tissue of interest.

The catheter 155 includes an interior lumen 163 defined by interior surfaces 165 of the catheter 155. The catheter 155 differs from a conventional catheter in that the catheter 155 has an interior surface 165 that is stepped at the distal end 157 to form a block retention pocket 159 that opens onto the distal end 157. The block retention pocket 159 includes an internal ledge 161 that is spaced a desired depth 167 from the distal end 157. The depth 167 may vary based on how much of the connector block 150 is to be held in the pocket 159. Optionally, the depth 167 may be great enough that the entire connector block 150 is recessed into the catheter 155 beyond the distal end 157.

The pocket 157 and connector block 150 include a keying feature 169, 171. For example, a bump or other raised projection 171 may be provided on the ledge 161, while a mating indent or notch 169 is provided in the proximal end 158 of the connector block 150. The projection 171 and notch 169 engage one another to prevent internal rotation of the connector block 150 within the catheter 155. For example, the physician may desire that the connector block 150 not rotate. The projection 171 and notch 169 cooperate to prevent rotation of the connector block 150. Alternatively, when a physician operates a user control to cause rotation of the distal end 157 of the catheter 155, the connector block 150 similarly rotates, thereby affording the physician detailed control over the rotational orientation of the connector block 150. As one example, when the physician causes the housing assembly 86 and/or electrode assembly 116 to rotate to screw in an active fixation member thereon, it may be desirable that the connector block 150 rotate by a similar amount to prevent entanglement of the wire segments 212, 210.

Optionally, the maneuvering wire 180 may be removed when the catheter 155 is used. Optionally, the catheter 155 may be omitted entirely and instead the wire 180 is used as the primary means to manipulate and adjust the connector block 150.

While not illustrated, it is understood that the components illustrated in FIG. 5A may be loaded into the electrode introducer assembly 110 or the housing introducer assembly 80, or into a separate introducer assembly (not shown). Optionally, the catheter 155 may be used in place of an introducer assembly.

Figure 5B:
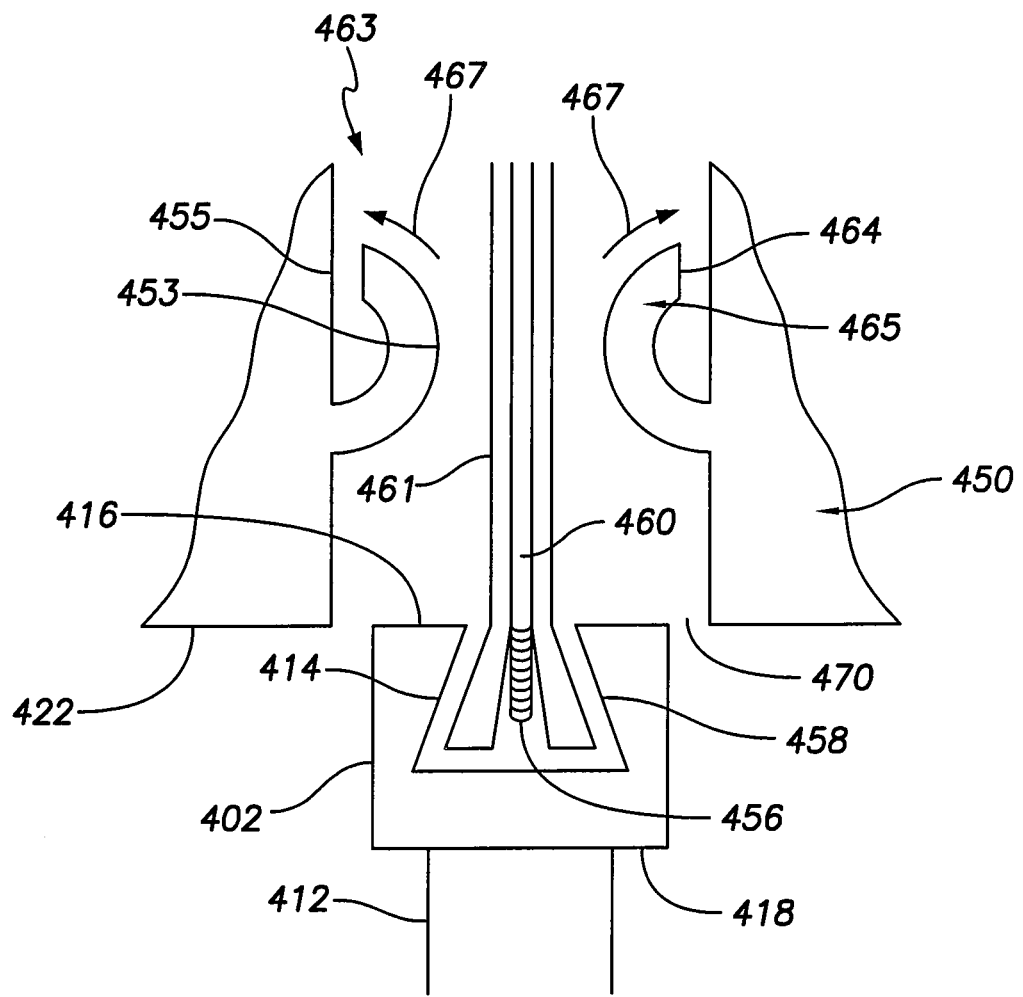
FIG. 5B illustrates a sectional view of detailed features of a connector block.

FIG. 5B illustrates an enlarged detail view of an alternative embodiment for a contact receiving member 463 within a connector block. In FIG. 5B, a portion of a connector block 450 is illustrated. The connector block 450 includes a distal end 422 with an opening 470 that communicates with a contact receiving member 463. The contact receiving member 463 includes opposed interior walls 455 having spring arms 465 provided thereon. The spring arms 465 are biased inward to a normal relaxed position (as shown in FIG. 5B). The spring arms 465 include rounded facing surfaces 453 that project into the open path through the contact receiving member 463. The spring arms 465 are deflectable in the direction of arrows 467 outward and away from one another.

In FIG. 5B, an end of a wire segment 412 is illustrated. The wire segment 412 may correspond to a housing assembly wire 94 or to an electrode assembly wire 124. The wire segment 412 includes a segment terminating contact 402 provided on the end thereof. The segment terminating contact 402 includes a mating end 416 and an opposed rear retention ledge 418. The mating end 416 includes a cavity with a tapered wall 414. The mating end 416 is configured to engage and deflect the spring arms 465 outward in the direction of arrows 467 as the segment terminating contact 402 is pulled into the contact receiving member 463. The segment terminating contact 402 moves to a position within the contact receiving member 463 at which the tips 464 of the spring arms 465 snap behind and under the ledge 418 to hold the contact 402 within the chamber 463.

In FIG. 5B, a stylet 461 is also illustrated. The stylet 461 includes a collet 458 provided on the outer end of the stylet 461. The stylet 461 also includes a central rod 460 that controls the collet 458. The collet 458 may be a sleeve with a (normally) cylindrical inner surface and a conical outer surface. The collet 458 is inserted into the cavity provided in the distal end 416 of the contact 402 and expanded against the matching tapered wall 414. The outer surface of the collet 458 expands to a slightly larger diameter, squeezing the tapered wall 414 of the contact 402. The rod 460 is operated to screw the threads 456 that cause the collet 458 to expand and contract.

Optionally, the collet 458 may be formed in a different manner, such that the collect enclosed the outer perimeter of the contact 402 and squeezes the outer surface of the contact 402 to grip the contact 402.

It should be recognized that the spring arms 465 may be used with various configurations of the contacts including the contacts 144, 148 illustrated in FIG. 5A. Similarly, the wire segment 412 and contact 402 may be used without the tapered wall 414. Instead, the wire segment 412 may include threaded channels and join to a wire similar to the channel 208 and wire 95 in the embodiment of FIG. 5A.

Figure 6:
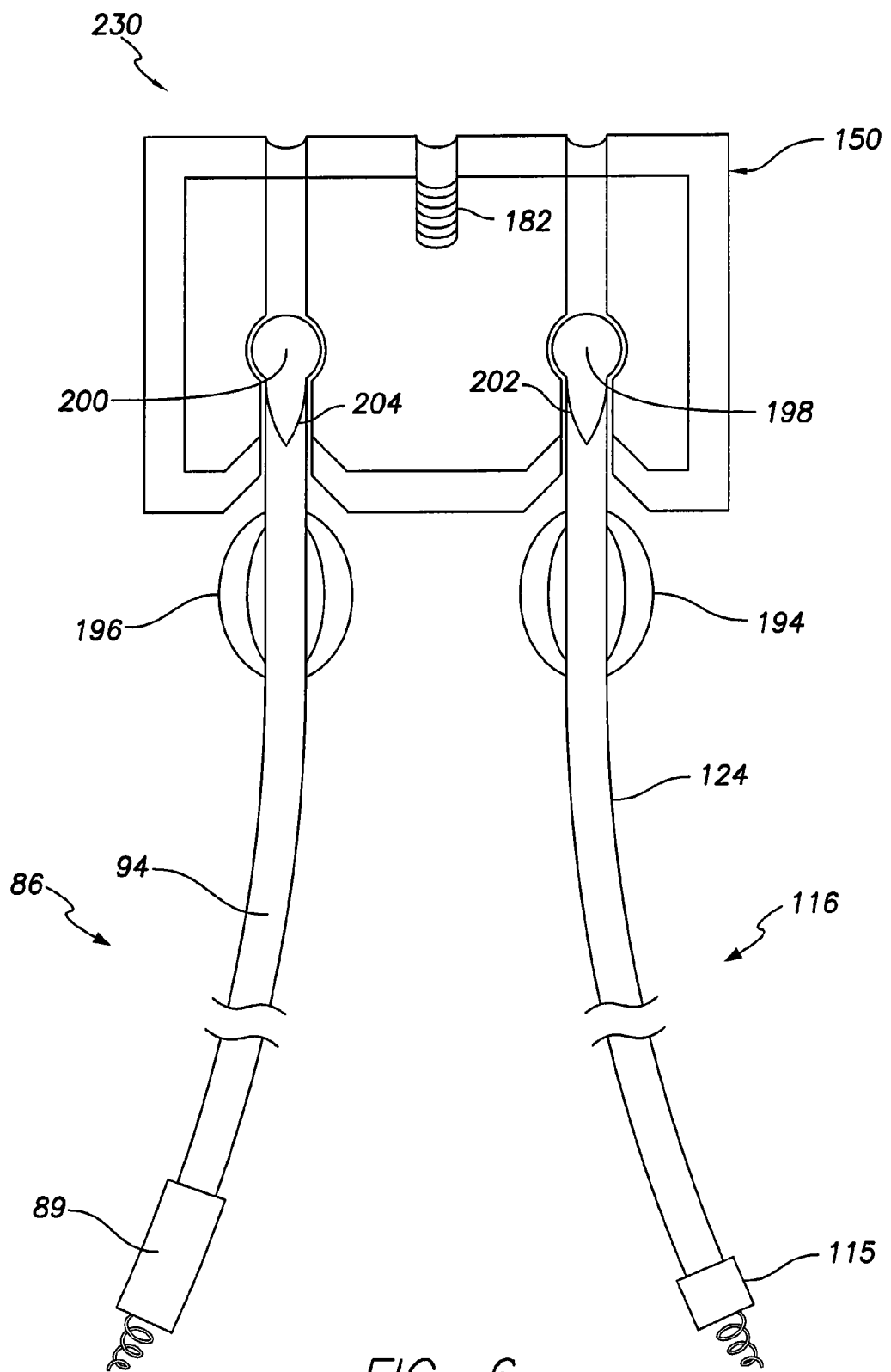
FIG. 6 illustrates a simplified view of an LIMD.

FIG. 6 illustrates a simplified view of a leadless intracardiac medical device (LIMD) 230, according to an embodiment. The device 230 includes a housing assembly 86 comprising a body 89 and a housing assembly wire 94, an electrode assembly 124 comprising a body 116 and an electrode assembly wire 124, and a connector block 150. The connector block 150 electrically connects components of the housing assembly 86 with components of the electrode assembly 116.

Figure 7:
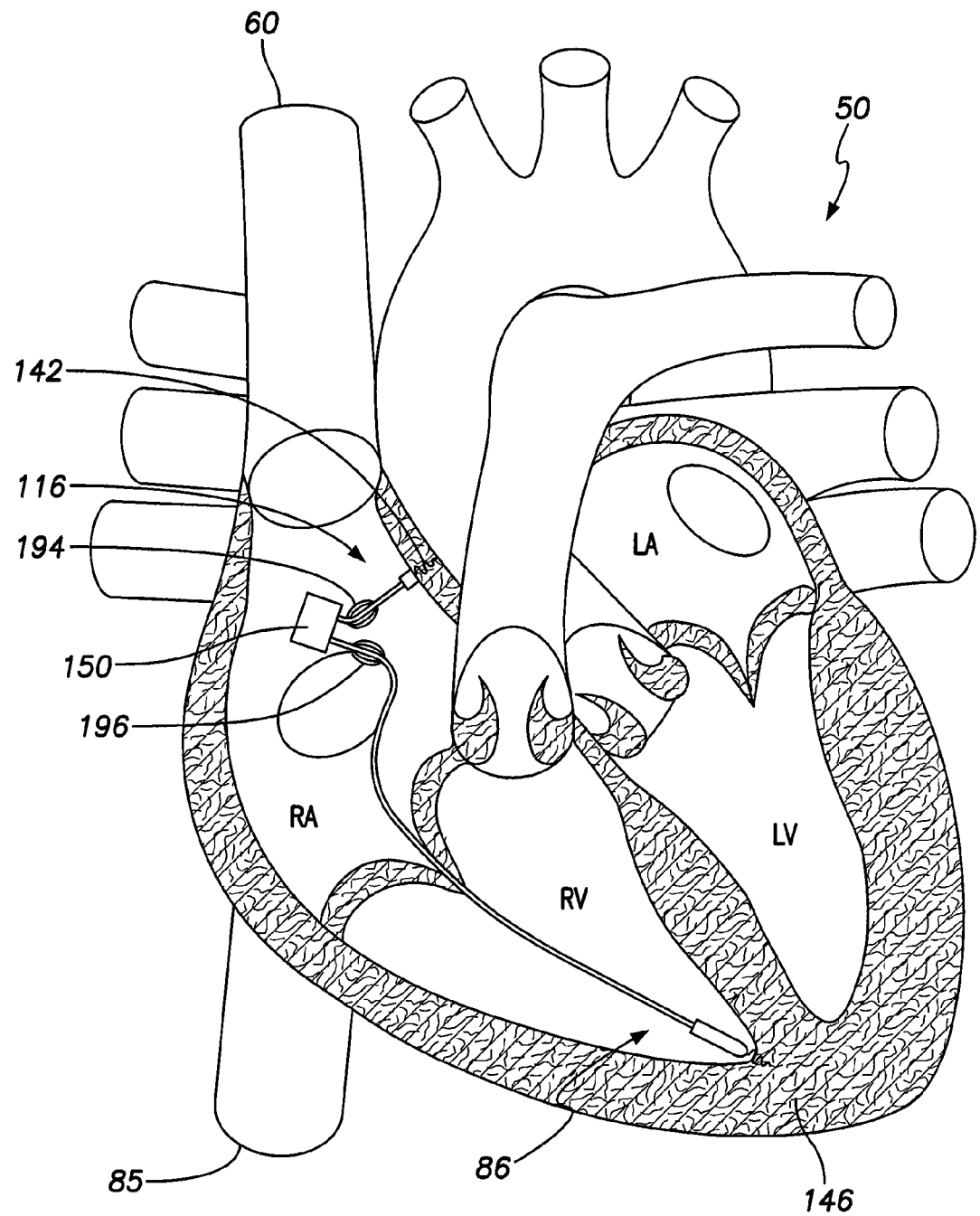
FIG. 7 illustrates a simplified view of an LIMD within a patient's heart.

FIG. 7 illustrates a simplified view of the LIMD 230 within the heart 50, according to an embodiment. As shown, the LIMD 230 is entirely within the heart 50. No portion of the device 230 is outside the heart 50. The device 230 may be programmed through the PSA 140 shown in FIG. 4. Alternatively, or additionally, the device 230 may be programmed through a telemetry unit.

Figure 8:
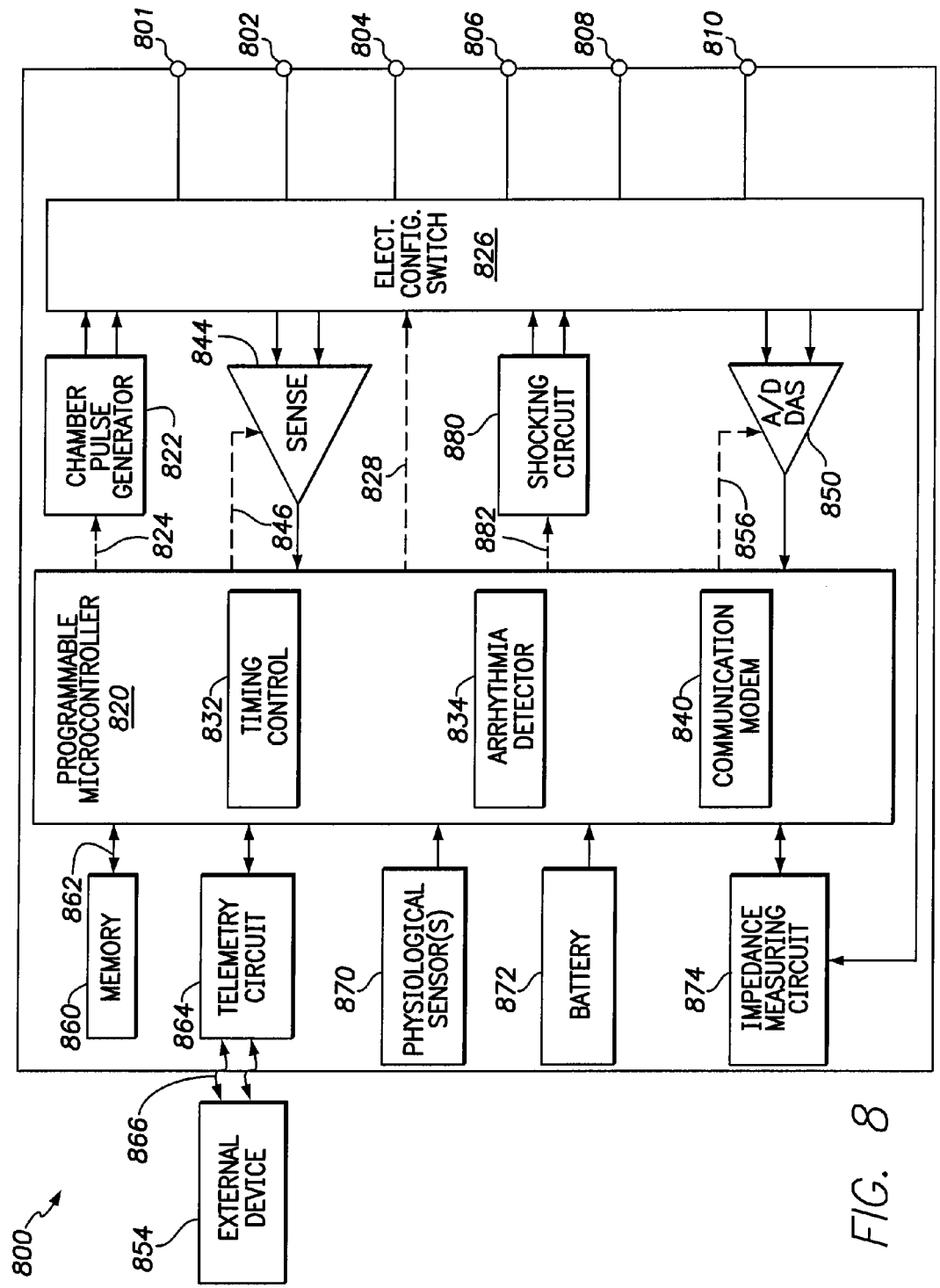
FIG. 8 illustrates an exemplary block diagram of the electrical components of an LIMD.

FIG. 8 shows an exemplary LIMD 800 configured for dual-chamber functionality from a primary location within a single side of the heart. For example, the LIMD 800 may be implemented as a pacemaker, equipped with both atrial and ventricular sensing and pacing circuitry. Alternatively, the LIMD 800 may be implemented with a reduced set of functions and components. For instance, the LIMD 800 may be implemented without ventricular sensing and pacing. The LIMD 800 may also be implemented with an increased set of functions. For example, if the LIMD 800 includes a coil type electrode, the LIMD may be configured to include cardioversion and/or shocking therapy capability.

The LIMD 800 has a housing 801 to hold the electronic/computing components. The housing 801 (which is often referred to as the "can", "case", "encasing", or "case electrode") may be programmably selected to act as the return electrode for certain stimulus modes. Electronics within the housing 801 further includes a plurality of terminals 802, 804, 806, 808, 810 that interface with electrodes of the LIMD. For example, the terminals may include: a terminal 802 that connects with a first electrode associated with the housing assembly (e.g. a helix electrode) and located in a first chamber; a terminal 804 that connects with a second electrode associated with the housing assembly (e.g., a ring electrode) and also located in the first chamber; a terminal 806 that connects with a third electrode associated with the electrode assembly (e.g. a helix electrode) and located in a second chamber; a terminal 808 that connects with a fourth electrode associated with the electrode assembly (e.g., a ring electrode); and an additional terminal, 810 that connect with one or more additional electrodes, if available. The type and location of each electrode may vary. For example, the electrodes may include various combinations of ring, tip, coil and shocking electrodes and the like.

The LIMD 800 includes a programmable microcontroller 820 that controls various operations of the LIMD 800, including cardiac monitoring and stimulation therapy. Microcontroller 820 includes a microprocessor (or equivalent control circuitry), RAM and/or ROM memory, logic and timing circuitry, state machine circuitry, and I/O circuitry.

LIMD 800 further includes a first chamber pulse generator 822 that generates stimulation pulses for delivery by one or more electrodes coupled thereto. The pulse generator 822 is controlled by the microcontroller 820 via control signal 824. The pulse generator 822 is coupled to the select electrode(s) via an electrode configuration switch 826, which includes multiple switches for connecting the desired electrodes to the appropriate I/O circuits, thereby facilitating electrode programmability. The switch 826 is controlled by a control signal 828 from the microcontroller 820.

In the example of FIG. 8, a single pulse generator 822 is illustrated. Optionally, the LIMD 800 may include multiple pulse generators, similar to pulse generator 822, where each pulse generator is coupled to one or more electrodes and controlled by the microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 800 includes sensing circuitry 844 selectively coupled to one or more electrodes through the switch 826. The sensing circuitry detects the presence of cardiac activity in the right chambers of the heart. The sensing circuitry 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 802 to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of the sensing circuitry 844 is connected to the microcontroller 820 which, in turn, triggers or inhibits the pulse generator 822 in response to the absence or presence of cardiac activity. The sensing circuitry 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

In the example of FIG. 8, a single sensing circuit 844 is illustrated. Optionally, the LIMD 800 may include multiple sensing circuit, similar to sensing circuit 844, where each sensing circuit is coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The LIMD 800 further includes an analog-to-digital (ND) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the LIMD 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 808 within each respective tier of therapy.

The operating parameters of the LIMD 800 may be non-invasively programmed into the memory 860 through a telemetry circuit 864 in telemetric communication via communication link 866 with the external device 854. The telemetry circuit 864 allows intracardiac electrograms and status information relating to the operation of the LIMD 800 (as contained in the microcontroller 820 or memory 860) to be sent to the external device 854 through the established communication link 866.

The IMD 802 can further include magnet detection circuitry (not shown), coupled to the microcontroller 820, to detect when a magnet is placed over the unit. A magnet may be used by a clinician to perform various test functions of the unit 802 and/or to signal the microcontroller 820 that the external programmer 854 is in place to receive or transmit data to the microcontroller 820 through the telemetry circuits 864.

The LIMD 800 may be equipped with a communication modem (modulator/demodulator) 840 to enable wireless communication with a remote device, such as a second implanted LIMD in a master/slave arrangement, such as described in U.S. Pat. No. 7,630,767. In one implementation, the communication modem 840 uses high frequency modulation. As one example, the modem 840 transmits signals between a pair of LIMD electrodes, such as between the can 800 and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller as a standalone component.

The LIMD 800 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and ventricular pacing pulses are administered. While shown as being included within the unit 802, the physiologic sensor(s) 870 may be external to the unit 802, yet still be implanted within or carried by the patient. Examples of physiologic sensors might include sensors that, for example, sense respiration rate, pH of blood, ventricular gradient, activity, position/posture, temperature, minute ventilation (MV), and so forth.

A battery 872 provides operating power to all of the components in the LIMD 800. The battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 872 also desirably has a predictable discharge characteristic so that elective replacement time can be detected. As one example, the unit 802 employs lithium/silver vanadium oxide batteries.

The LIMD 800 further includes an impedance measuring circuit 874, which can be used for many things, including: impedance surveillance during the acute and chronic phases for proper LIMD positioning or dislodgement; detecting operable electrodes and automatically switching to an operable pair if dislodgement occurs; measuring respiration or minute ventilation; measuring thoracic impedance; detecting when the device has been implanted; measuring stroke volume; and detecting the opening of heart valves; and so forth. The impedance measuring circuit 874 is coupled to the switch 826 so that any desired electrode may be used.

The microcontroller 820 further controls a shocking circuit 880 by way of a control signal 882. The shocking circuit 880 generates shocking pulses of low (e.g., up to 0.5 joules), moderate (e.g., 0.5-10 joules), or high energy (e.g., 811 to 40 joules), as controlled by the microcontroller 820. Such shocking pulses are applied to the patient's heart 808 through shocking electrodes, if available on the LIMD. It is noted that the shock therapy circuitry is optional and may not be implemented in the LIMD, as the various LIMDs described above and further below will typically not be configured to deliver high voltage shock pulses. On the other hand, it should be recognized that an LIMD may be used within a system that includes backup shock capabilities, and hence such shock therapy circuitry may be included in the LIMD.

Figure 9:
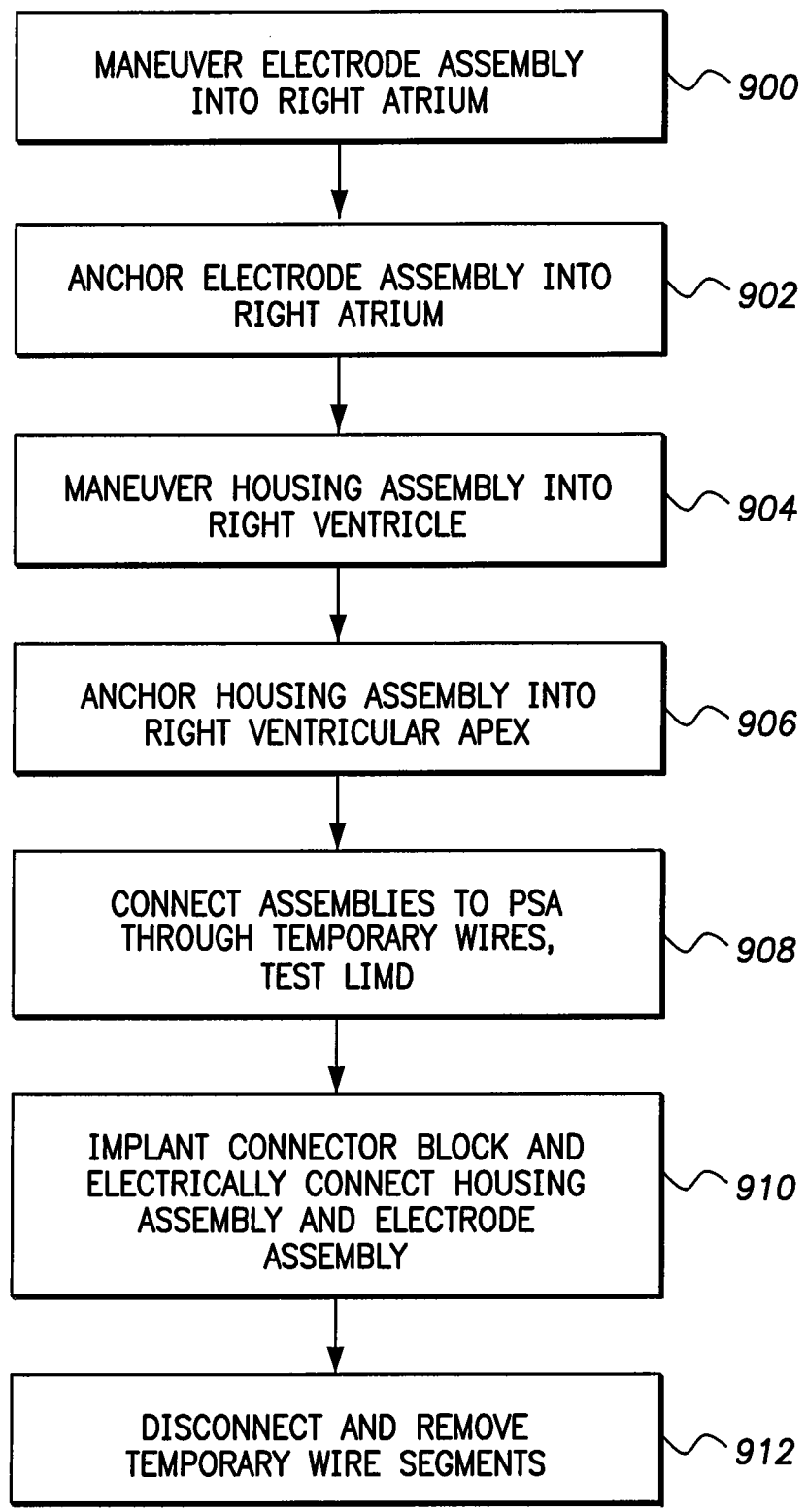
FIG. 9 illustrates a flow chart of a process of implanting a LIMD.

FIG. 9 illustrates a flow chart of a process of implanting an LIMD, according to an embodiment. At 900, an electrode assembly 116 with a temporary electrode wire segment 125 attached thereto is maneuvered into a right atrium of a heart. The electrode assembly 116 may be positioned as such using an electrode introducer assembly 110, as described above. The electrode assembly 116 is maneuvered into a patient's vein, through the inferior or superior vena cava, and into the heart to arrive at the right atrium of the heart.

At 902, the electrode assembly 116 is anchored into the right atrium. For example, the electrode assembly 116 may be anchored into the right atrial appendage, as explained above. Once the electrode assembly 116 is anchored, the electrode introducer assembly 110 is withdrawn, leaving the electrode assembly with a temporary electrode wire segment 125 attached, implanted in the heart.

Next, at 904, a housing assembly 86 with a temporary housing assembly wire 95 is maneuvered into the right ventricle. The housing assembly 86 may be positioned as such using a housing introducer assembly 80, as described above. At 906, the housing assembly 86 is anchored into the right ventricular apex. Once the housing assembly 86 is anchored in place, the housing introducer assembly 80 is withdrawn, leaving the housing assembly with a temporary electrode wire segment 95 attached, implanted in the heart. Notably, the housing assembly may be maneuvered and anchored before (or even at the same time as) the electrode assembly.

At 908, the terminal ends of the temporary electrode wire segment 125 and temporary housing wire segment 95 are attached to a PSA and the functionality of the LIMD is tested. At completion of testing, the temporary wire segments are disconnected from the PSA. At 910, a connector block 150 is placed over the temporary wire segments 95, 125 and the connector block is then maneuvered over the wires into the heart as described above with reference to FIG. 5A. The connector block 150 is advanced to engage the segment-terminating contacts 144, 148 of the housing assembly wire 94 and the electrode assembly wire 124 to thereby establish electrical connection between the assemblies.

At 912, the temporary wire segments 95, 125 are disconnected from the assembly wires 94, 124 and removed, thereby leaving the LIMD fully-functioning within the heart.

Thus, embodiments provide a pacing device configured to be entirely within a heart of a patient, and a method of implanting the same. Embodiments provide a device and method for dual chamber pacing, such as DDDR pacing, without leads that connect a device that is external to the heart. Unlike a conventional IMD, embodiments provide a device that has no components outside the heart, thereby providing: a low infection rate, elimination of Twiddler's syndrome, greater patient comfort, little or no skin erosion, and elimination of other problems associated with conventional pacemaker implantation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A leadless intra-cardiac medical device (LIMD) configured to be contained within a heart of a patient, said device comprising:

an electrode assembly configured to be retained completely within the heart of the patient and further configured to be anchored within a first wall portion of a first chamber of a heart, the electrode assembly comprising an electrode main body having a first securing helix, an electrode wire segment extending from the body and a first segment-terminating contact positioned on the electrode wire segment, the first securing helix configured to be anchored within a first wall portion of the first chamber of a heart;

a housing assembly configured to be retained completely within the heart of the patient and further configured to be anchored within a second wall portion of a second chamber of the heart, the housing assembly comprising a body having a second securing helix and a housing wire segment extending from the body, and a second segment-terminating contact positioned on the housing wire segment;

a connector block having a first side and a second side, the connector block having first and second passages extending from the first side to the second side, through the connector block, the connector block having a first flared chamber along the first passage and intermediate the first side and second side and a second flared chamber along the second passage and intermediate the first sided and the second side, the connector block further having a threaded opening positioned along the first edge and intermediate the first and second passages, the threaded opening to receive therein a maneuvering wire; and the connector block further for retaining, in the first passage, the first segment-terminating contact on the electrode wire segment extending from the body of the electrode assembly and for retaining, in the second passage, the second segment-terminating contact on the housing wire segment extending from the body of the housing assembly, the connector further electrically splicing together the electrode wire segment extending from the body of the electrode assembly with the housing wire segment extending from the body of the housing assembly to electrically connect the electrode wire segment to the housing wire segment by retaining the first and second segment-terminating contacts.

2. The device of claim 1, wherein the housing wire segment is configured to extend into the first chamber and terminate therein.

3. The device of claim 1, wherein the electrode wire segment is configured to terminate within the first chamber.

4. The device of claim 1, wherein the first segment-terminating contact extends into the first passage and is securely retained in the first flared chamber and the second-terminating contact extends into the second passage and is securely retained in the second flared chamber.

5. The device of claim 1, wherein each of the first and second segment-terminating contacts comprises a connection stud that is retained within the first and second flared chambers of the connector block.

6. The device of claim 5, wherein each of the connection studs comprises an expanded head integrally connected to a clamping tail.

7. The device of claim 1, wherein at least one of the first and second segment-terminating contacts includes a recess configured to be temporarily connected to a pacing system analyzer wire segment during implantation.

8. The device of claim 1, wherein the first and second wire-terminating contacts being inserted into the first and second passages through the first side, the connector block configured to receive pacing system analyzer wire segments into the first and second passages through the second side.

9. The device of claim 1, wherein the first and second passages of the connector block join contact receiving terminals.

10. A leadless intra-cardiac medical device (LIMD) configured to be contained within a heart of a patient, said device comprising:
   an electrode assembly configured to be retained completely within the heart of the patient and further configured to be anchored within a first wall portion of a first chamber of a heart, the electrode assembly comprising an electrode main body having a first securing helix, an electrode wire segment extending from the body and a first segment-terminating contact positioned on the electrode wire segment, the first securing helix configured to be anchored within a first wall portion of the first chamber of a heart;
   a housing assembly configured to be retained completely within the heart of the patient and further configured to be anchored within a second wall portion of a second chamber of the heart, the housing assembly comprising a body having a second securing helix and a housing wire segment extending from the body, and a second segment-terminating contact positioned on the housing wire segment; and
   a connector block having an electrically conductive main body, the connector block having a first side and a second side, the connector block having first and second passages being directly electrically coupled by the electrically conductive material of the main body, the first and second passages extending from the first side to the second side, through the connector block, the connector block having a first flared chamber along the first passage and intermediate the first side and second side, the connector block further having a threaded opening positioned along the first edge and intermediate the first and second passages, the threaded opening to receive therein a maneuvering wire; and
   the connector block further for retaining, in the first passage, the first segment-terminating contact on the electrode wire segment extending from the body of the electrode assembly and for retaining, in the second passage, the second segment-terminating contact on the housing wire segment extending from the body of the housing assembly, the connector further electrically splicing together the electrode wire segment extending from the body of the electrode assembly with the housing wire segment extending from the body of the housing assembly to electrically connect the electrode wire segment to the housing wire segment by retaining the first and second segment-terminating contacts.

11. The device of claim 10, wherein the connector block further includes a second flared chamber along the second passage and intermediate the first sided and the second side.

12. The device of claim 11, wherein the housing wire segment is configured to extend into the first chamber and terminate therein.

13. The device of claim 12, wherein the electrode wire segment is configured to terminate within the first chamber.

14. The device of claim 13, wherein the first segment-terminating contact extends into the first passage and is securely retained in the first flared chamber and the second-terminating contact extends into the second passage and is securely retained in the second flared chamber.

15. The device of claim 14, wherein each of the first and second segment-terminating contacts comprises a connection stud that is retained within first and second flared chambers of connector block.

16. The device of claim 15, wherein each of the connection studs comprises an expanded head integrally connected to a clamping tail.

17. The device of claim 16, wherein at least one of the first and second segment-terminating contacts includes a recess configured to be temporarily connected to a pacing system analyzer wire segment during implantation.

18. The device of claim 17, wherein the first and second wire-terminating contacts being inserted into the first and second passages through the first side of the connector block, the connector block configured to receive pacing system analyzer wire segments into the first and second passages through the second side of the connector block.

19. The device of claim 18, wherein the first and second passages of the connector block join contact receiving terminals.

* * * * *